United States Patent
Connors et al.

(12)

(10) Patent No.: US 7,524,328 B2
(45) Date of Patent: *Apr. 28, 2009

(54) RADIATION DELIVERY MODULE AND DERMAL TISSUE TREATMENT METHOD

(75) Inventors: Kevin P. Connors, San Francisco, CA (US); Michael W. Sasnett, Los Altos, CA (US)

(73) Assignee: Cutera, Inc., Brisbane, CA (US)

( * ) Notice: Subject to any disclaimer, the term of this patent is extended or adjusted under 35 U.S.C. 154(b) by 564 days.

This patent is subject to a terminal disclaimer.

(21) Appl. No.: 10/389,260

(22) Filed: Mar. 14, 2003

(65) Prior Publication Data

US 2004/0015157 A1  Jan. 22, 2004

Related U.S. Application Data

(63) Continuation of application No. 09/524,077, filed on Mar. 13, 2000, now Pat. No. 6,569,155.

(60) Provisional application No. 60/124,709, filed on Mar. 15, 1999.

(51) Int. Cl.
*A61N 5/067* (2006.01)

(52) U.S. Cl. .......................... 607/89; 607/88
(58) Field of Classification Search ............. 607/88–94; 606/2–3, 9–19, 1
See application file for complete search history.

(56) References Cited

U.S. PATENT DOCUMENTS 3,538,919 A   11/1970   Meyer .......................... 606/36
3,693,623 A   9/1972   Harte et al. ..................... 606/9
3,834,391 A   9/1974   Block .............................. 606/9
3,900,034 A   8/1975   Katz et al. ..................... 607/89
4,122,853 A   10/1978   Smith ............................. 606/4

(Continued)

FOREIGN PATENT DOCUMENTS

EP           0130950      *   3/1984

(Continued)

OTHER PUBLICATIONS

R. Anderson, *Harvard Medical School, Reprint* "Clinical Use of the LightSheer Diode Laser System," Mar. 1998.

(Continued)

*Primary Examiner*—Roy D Gibson
(74) *Attorney, Agent, or Firm*—Morrison & Foerster LLP

(57) ABSTRACT

A radiation delivery module (8) includes a body (48) supportable on a patient's skin and defines a skin surface plane generally aligned with the patient's skin surface (40). A radiation source (22) is mounted to the body and produces a beam (34) of tissue-damaging radiation directed transverse to and at the skin surface plane. The radiation beam creates a radiation spot (42) having a length (36) and a width (44) at the skin surface plane, the length being at least about 5 to 10 times the width. A number of scanned diode laser radiation sub-sources (64) each directing a radiation beam component (66) at the radiation spot may be used. The radiation source may include a rod lens as a focusing optical element. The radiation delivery module may also include a radiation source translator (18) so that the radiation spot moves in a direction generally perpendicular to the length of the radiation spot.

8 Claims, 5 Drawing Sheets

U.S. PATENT DOCUMENTS

| | | | |
|---|---|---|---|
| 4,388,924 A | 6/1983 | Weissman et al. | 606/9 |
| 4,461,294 A | 7/1984 | Baron | 606/5 |
| 4,608,978 A | 9/1986 | Rohr | 606/9 |
| 4,617,926 A | 10/1986 | Sutton | 606/9 |
| 4,733,660 A | 3/1988 | Itzkan | 606/9 |
| 4,819,669 A | 4/1989 | Politzer | 132/200 |
| 4,829,262 A | 5/1989 | Furumoto | 359/346 |
| 4,917,084 A | 4/1990 | Sinofsky | 606/7 |
| 5,000,752 A | 3/1991 | Hoskin et al. | 606/9 |
| 5,057,104 A | 10/1991 | Chess | 606/9 |
| 5,059,192 A | 10/1991 | Zaias | 606/9 |
| 5,067,817 A * | 11/1991 | Glenn | 356/613 |
| 5,090,798 A | 2/1992 | Kohayakawa | 351/221 |
| 5,178,617 A | 1/1993 | Kuizenga et al. | 606/17 |
| 5,182,857 A | 2/1993 | Simon | 30/34.05 |
| 5,217,455 A | 6/1993 | Tan | 606/9 |
| 5,226,907 A | 7/1993 | Tankovich | 606/133 |
| 5,258,989 A | 11/1993 | Raven | 372/6 |
| 5,282,797 A | 2/1994 | Chess | 606/9 |
| 5,290,273 A | 3/1994 | Tan | 606/9 |
| 5,304,170 A | 4/1994 | Green | 606/9 |
| 5,312,395 A | 5/1994 | Tan et al. | 606/9 |
| 5,336,217 A * | 8/1994 | Buys et al. | 606/9 |
| 5,344,418 A | 9/1994 | Ghaffari | 606/9 |
| 5,397,327 A | 3/1995 | Koop et al. | 606/17 |
| 5,405,368 A | 4/1995 | Eckhouse | 607/88 |
| 5,411,502 A | 5/1995 | Zair | 606/10 |
| 5,425,728 A | 6/1995 | Tankovich | 606/9 |
| 5,474,549 A | 12/1995 | Ortiz et al. | 606/9 |
| 5,486,172 A | 1/1996 | Chess | 606/20 |
| 5,522,813 A | 6/1996 | Trelles | 606/2 |
| 5,527,350 A | 6/1996 | Grove et al. | 607/89 |
| 5,546,214 A | 8/1996 | Black et al. | 359/203 |
| 5,582,752 A | 12/1996 | Zair | 219/121.85 |
| 5,611,795 A | 3/1997 | Slatkine et al. | 606/9 |
| 5,620,478 A | 4/1997 | Eckhouse | 607/88 |
| 5,626,631 A * | 5/1997 | Eckhouse | 607/88 |
| 5,683,380 A | 11/1997 | Eckhouse et al. | 606/9 |
| 5,735,844 A | 4/1998 | Anderson et al. | 606/9 |
| 5,738,679 A | 4/1998 | Daikuzono | 606/11 |
| 5,743,901 A * | 4/1998 | Grove et al. | 606/9 |
| 5,820,625 A | 10/1998 | Izawa et al. | 606/9 |
| 5,957,915 A | 9/1999 | Trost | 606/13 |
| 5,957,960 A | 9/1999 | Chen et al. | 607/92 |
| 5,964,749 A | 10/1999 | Eckhouse et al. | 606/9 |
| 6,080,147 A | 6/2000 | Tobinick | 606/9 |
| 6,168,590 B1 * | 1/2001 | Neev | 606/9 |
| 6,210,425 B1 | 4/2001 | Chen | 607/88 |
| 6,235,015 B1 * | 5/2001 | Mead et al. | 606/9 |
| 6,251,127 B1 | 6/2001 | Biel | 607/88 |
| 6,237,884 B1 | 8/2001 | Altshuler et al. | 606/9 |
| 6,273,884 B1 * | 8/2001 | Altshuler et al. | 606/9 |
| 6,273,885 B1 | 8/2001 | Koop et al. | 606/9 |
| 6,383,176 B1 * | 5/2002 | Connors et al. | 606/9 |
| 6,569,155 B1 * | 5/2003 | Connors et al. | 606/9 |
| 6,887,233 B2 | 5/2005 | Angeley et al. | 606/17 |
| 6,951,558 B2 | 10/2005 | Angeley et al. | 606/18 |

FOREIGN PATENT DOCUMENTS

| | | |
|---|---|---|
| EP | 736 308 | 10/1996 |
| WO | WO 86/02783 | 5/1986 |
| WO | WO 95/15725 | 6/1995 |
| WO | WO 96/22813 | 8/1996 |
| WO | WO 98/24514 | 6/1998 |
| WO | WO 98/51235 | 11/1998 |
| WO | WO 99/11324 | 3/1999 |

OTHER PUBLICATIONS

Bartley et al., "An Experimental Study to Compare Methods of Eyelash Ablation," *Ophthalmology*, vol. 94, 1987, pp. 1286-1289.

J.L. Boulnois, "Photophysical Processes in Recent Medical Laser Developments: a Review," *Lasers in Medical Science*, vol. 1, 1986, pp. 47-64.

Finkelstein et al., "Epilation of Hair-Bearing Urethral Grafts Using the Neodymium:YAG Surgical Laser," *J. Urology*, vol. 146, 1991, pp. 840-842.

Grossman et al., "Prospective Evaluation of the Argon Laser in the Treatment of Trichiasis," *Ophthalmic Surgery*, vol. 23, 1992, pp. 183-189.

Grossman et al., "Experimental Comparison of Laser and CryoSurgical Cilia Destruction," *Ophthalmic Surgery*, vol. 23, 1992, pp. 179-182.

Kuriloff et al., "Pharyngoesophageal Hair Growth: the role of Laser Epilation,": *Case Reports*, vol. 98, 1988, pp. 342-345.

\* cited by examiner

RADIATION DELIVERY MODULE AND DERMAL TISSUE TREATMENT METHOD

CROSS-REFERENCE TO RELATED APPLICATIONS

This claims the benefit of U.S. Provisional Patent Application No. 60/124,709, filed Mar. 15, 1999 entitled Hair Removal System Using Scanned Diode Laser. This also is related to U.S. patent application Ser. No. 09/393,830, now U.S. Pat. No. 6,485,484, filed Sep. 10, 1999 entitled Hair Removal Device. This application is a continuation of U.S. application Ser. No. 09/524,077, now U.S. Pat. No. 6,569,155, filed Mar. 13, 2000.

BACKGROUND OF THE INVENTION

Use of light to denature very specific kinds of tissue has been called wavelength-selective photo-thermolysis. The use of lasers for this purpose has been well described in the literature. See, for example, R. G. Wheland, "Laser-assisted hair removal", *Lasers in Dermatology*, Vol. 15, pp. 469-477, and references cited. By choosing a laser with the right wavelength and energy per unit area (fluence), a particular light-absorbing target substance (chromophore) in living tissue, such as melanin or possibly hemoglobin, will absorb energy from the treatment beam and become hot enough to destroy functionality in the tissue containing the chromophore. Tissue in the same area that does not have high concentration of the target chromophore will not be as affected.

Hair H, see FIG. 1C, includes two basic parts, the shaft S, which is the portion of the hair above the epidermis E, and the root R, which is the portion below the surface of the epidermis. Various tissues surround the root of the hair. Hair color is primarily due to the presence of melanin in the hair. Melanin is created at the base of the hair follicle F and is passed into the hair as it grows. The presence of melanin has made it possible to use certain lasers and other light sources for hair removal with melanin as the target chromophore. The hair follicle and surrounding structure (referred to collectively as hair tissue T) are selectively heated when the melanin in the hair tissue and in the hair root itself and is exposed to treatment radiation. The hair tissue is thermally damaged as a result of the localized heating after treatment; many of the exposed hairs atrophy and are sloughed from the epidermis.

The early work in this field was centered around a wavelength with very high melanin absorption, the pulsed ruby laser (694 nm). Long pulse ruby lasers (as opposed to Q-switched ruby lasers) typically have a pulse duration, or a series of pulses, in the 1 millisecond range. Although the wavelength is highly absorbed in melanin, the wavelength selection has significant limitations with darker skin types as the epidermis can blister or induce a pigmentary change from the superficial melanin heating.

Dermatologists have used cooling devices in dermatologic applications prior to laser treatment. The purpose is to chill the skin with the understanding that exposure to treatment radiation will elevate the epidermal temperature. Chilling lowers the initial temperature so that the post treatment temperature at the epidermis will not create a heat-induced blister or pigmentary change. U.S. Pat. No. 5,735,844 describes apparatus which uses a cooled lens, through which radiation passes, pressed against the patient's skin to cool the epidermis.

Many different approaches to hair removal have been explored since the early ruby laser evaluation. A common trend is a continual shift towards longer wavelengths, which have less melanin absorption, as it allows treatment of patients with a darker range of skin tones. Initially, alexandrite (755 nm) was evaluated and later a diode approach (810 nm). The alexandrite laser offers some improved clinical capabilities over the ruby laser if one considers treatment of darker skin types. However, from engineering and system performance measures, the two systems are similar in terms of size, utility requirement, treatment speed, and system cost. In contrast, the high pulse energy diode laser allows the system to be much smaller than previous systems with an ability to run off of standard power. A high pulse energy diode has many attractive attributes over other laser approaches, such as flashlamp excited solid-state devices and therapeutic filtered flashlamps. One of the most desirable traits is the high efficiency associated with diode generated laser radiation. As a result of improved efficiency, the system can be smaller and lighter weight.

One of the performance limitations working against a diode laser for an application like hair removal is the need for high peak power for short bursts. In general, diode lasers may be pulsed at peak power levels higher than the rated continuous power. However, the peak rating is not a significantly higher power level (perhaps two to three times) than the continuous level. A constraint that a hair removal application has is the need to deliver significant energy deep into the dermis to sufficiently heat the hair tissue to induce a thermal injury so that the hair will slough off. Light scatters as it propagates through the tissue. As a result of this severe exposure, large area treatments (greater than 20 mm$^2$) have been explored to overcome the reduction (due to scatter) in intensity as the light travels deeper into the dermis. A large treatment area can generate a fairly homogeneous intensity profile under the center of the treatment area as light propagates into the dermis.

A commercially-available diode laser system for hair removal is sold by Coherent of Santa Clara, Calif. as Lightsheer and allows the physician to treat the darker skin types than ruby lasers with a lower risk of post operative blistering. The Lightsheer system employs many diode bars (between 50 to 100) to create high peak power (2-4 kW) and a large square treatment area (about 0.81 cm$^2$). The Lightsheer system is used in pulsed operation with treatment rates up to about 1.6 cm$^2$/sec. The system has a pulse duration between 5 and 30 ms, which closely matches the thermal relaxation time of typical hair follicles.

SUMMARY OF THE INVENTION

A radiation delivery module includes a body supportable on a skin surface of a patient to define a skin surface plane. A radiation source is mounted to the body and produces a beam of tissue-damaging radiation directed transverse to and at the skin surface plane. The radiation beams creates a radiation spot having a length and a width at the skin contacting plane, the length preferably being about 10 or more times, but at least about 5 times, the width. A number of radiation sources, each directing a radiation beam component at the radiation spot, may be used. The radiation source may include a rod lens as a focusing optical element. The radiation delivery module may also include means for translating the radiation source so that the radiation spot moves in a direction generally perpendicular to the length of the radiation spot.

Another aspect of the invention relates to a method for treating dermal tissue. A tissue-damaging radiation beam is directed the skin of a patient to create a radiation spot on the skin having a length of preferably about 10 or more times, but at least about 5 times, its width. The radiation beam is moved along the skin in a direction transversed to the length. The directing step may be carried out with the radiation beam having a focal point located below the skin surface. The radiation beam is preferably moved in a direction which is perpendicular to the length of the radiation spot. The invention may be carried out using a radiation delivery module, including a body carrying a translatable radiation source, positioned at a chosen location on the skin surface of the patient. The radiation source may be moved relative to the body while the body is stationary relative to the skin surface. A number of radiation sub-sources, each producing a radiation beam component, may be used to produce the radiation beam. The radiation beam may be produced using a diode laser.

Other features and advantages of the invention will appear from the following description in which the preferred embodiment has been set forth in detail in conjunction with the accompanying drawings.

DESCRIPTION OF THE SPECIFIC EMBODIMENTS

Figure 1:
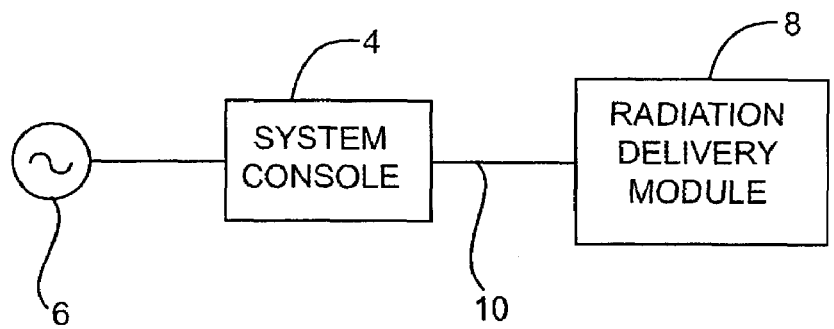
FIG. 1 is a simplified schematic view of a radiation delivery system made according to the invention.
Figure 1A:
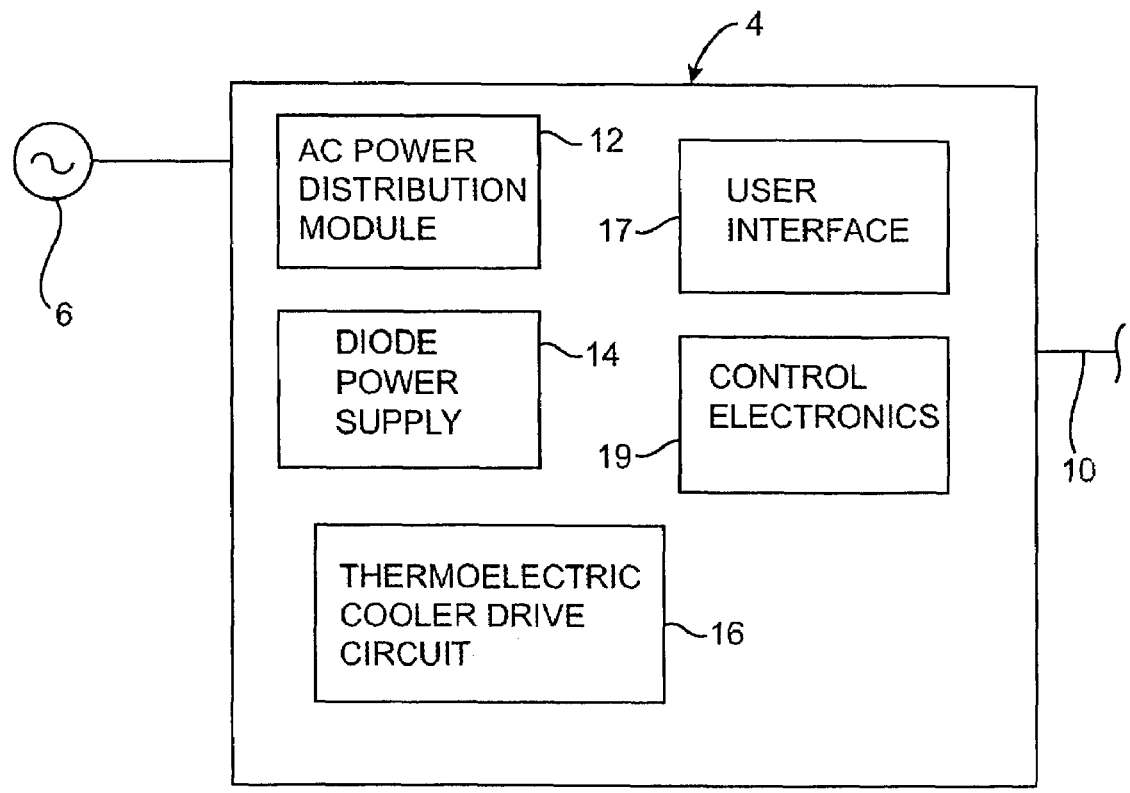
FIGS. 1A and 1B are schematic representations of the main components of the system console and the radiation delivery module of FIG. 1.
Figure 1B:
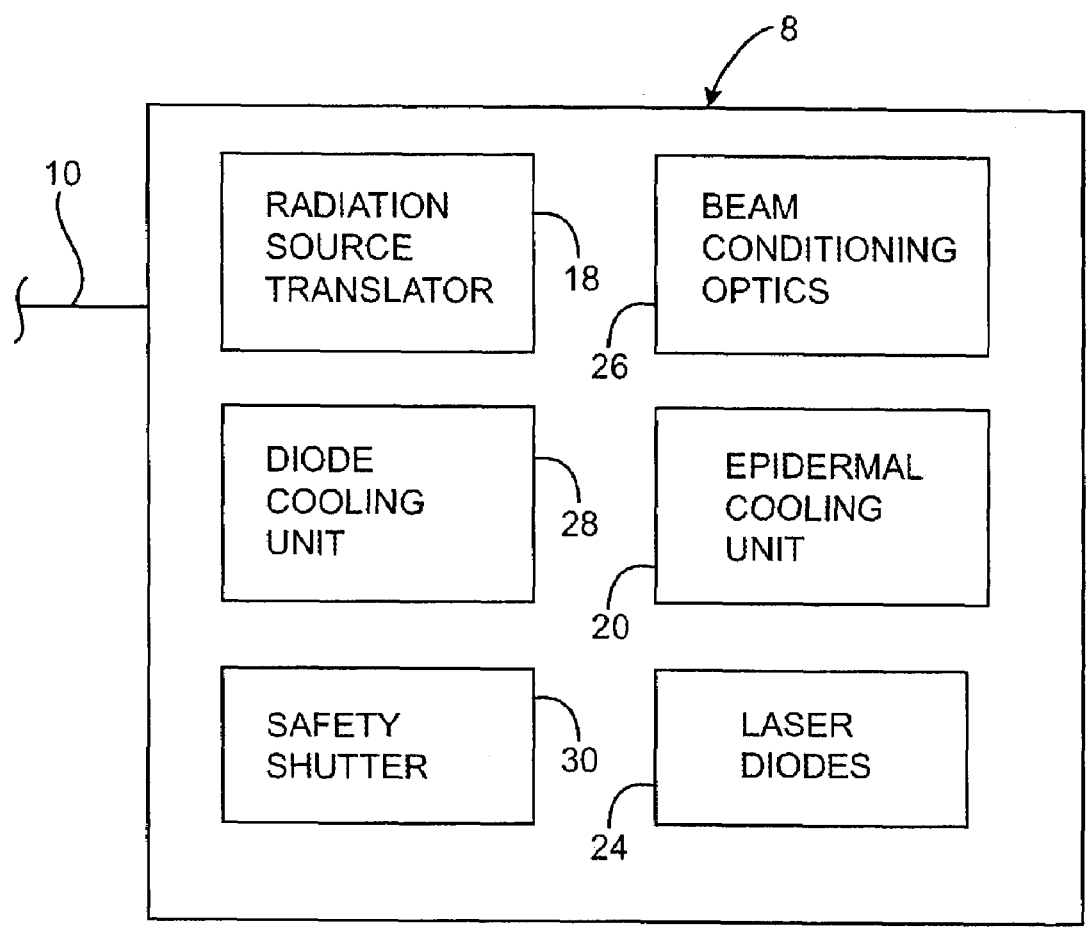
Figure 1C:
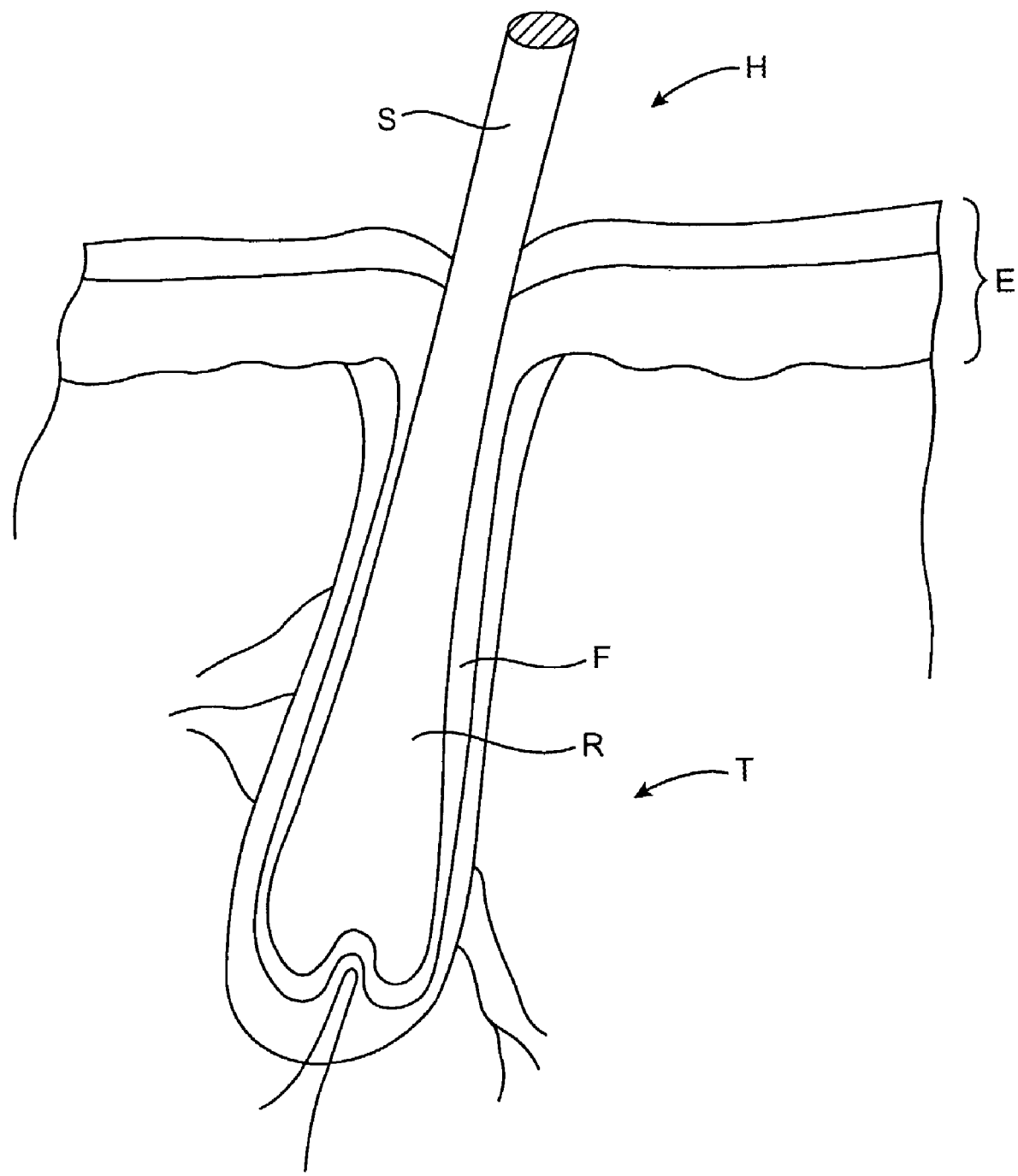
FIG. 1C is a simplified cross-sectional view of a hair with its root within a hair follicle.

FIGS. 1, 1A and 1B illustrate a radiation delivery system 2 in schematic form. System 2 includes broadly a system console 4 coupled to a power source 6, and a radiation delivery module 8 coupled to system consoles 4 by an umbilical cable 10. System console 4 can be generally conventional in construction and typically includes an AC power distribution module 12, a high current diode power supply 14, a thermolelectric cooler drive circuit 16, a user interface 17 and control electronics 19. The components of system console 4 are typically generally conventional in construction, form no part of this invention and will not be described further.

Figure 2:
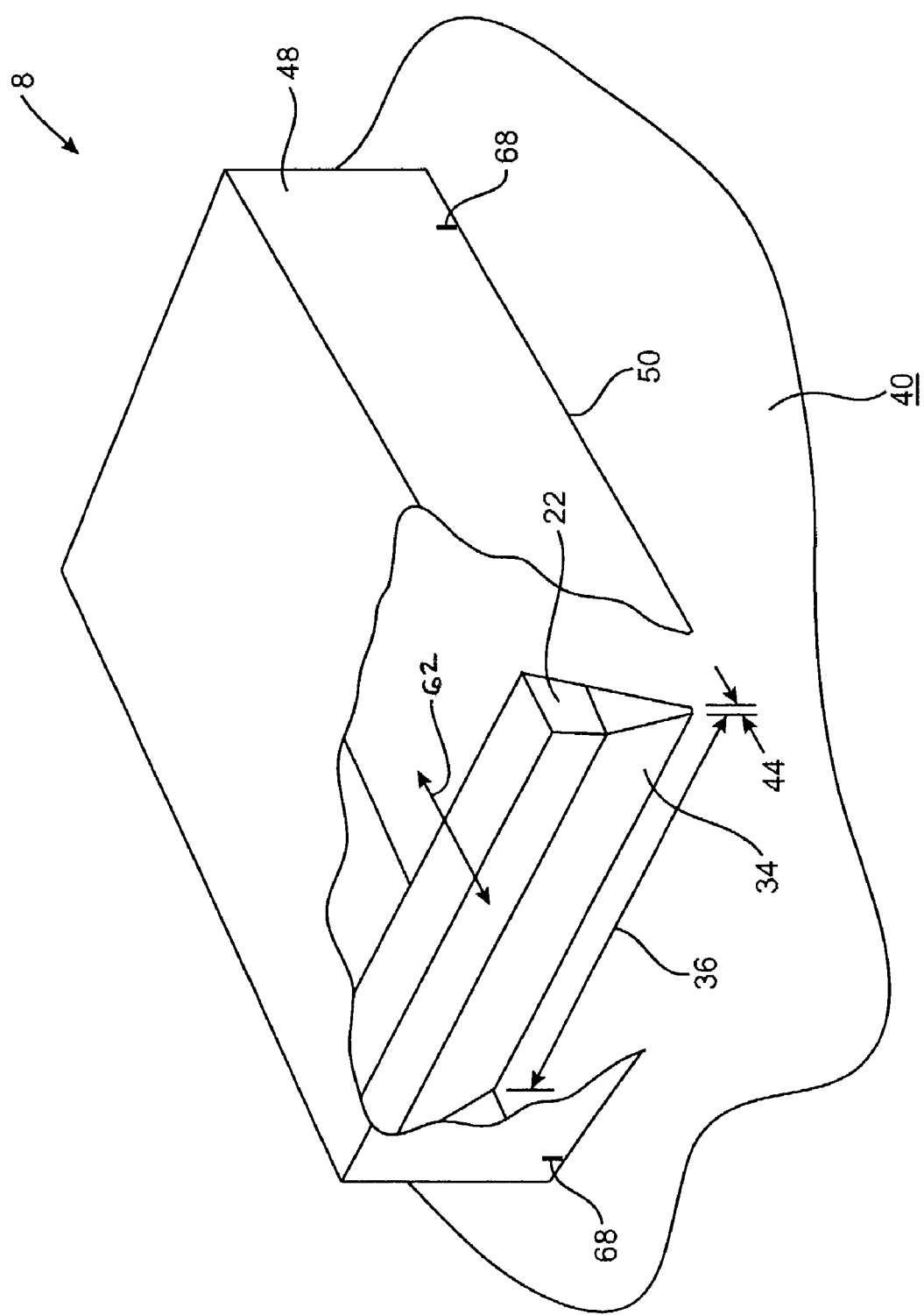
FIG. 2 illustrates, in simplified form, an overall view of the radiation delivery module of FIG. 1 resting on a skin surface of a patient.

FIG. 1B illustrates in schematic form radiation delivery module 8 seen to include a radiation source translator 18, an epidermal cooling unit 20 (not shown in any other figure), and four components constituting the radiation source 22 shown in FIG. 2. Radiation source 22 includes a number of laser diodes 24, beam conditioning optics 26, diode cooling unit 28 (shown only in FIG. 1B), and safety shutter 30(shown only in FIG. 1B). While in the preferred embodiment several laser diodes are used, to simplify the discussion, FIGS. 1B, 2 and 3 will be discussed with reference to only a single laser diode.

Radiation source translator 18 is used to control the dwell time on tissue. Cooling of the patient's skin before and/or after being irradiated by epidermal cooling unit 20 can help prevent undesirable tissue damage and reduce pain. Examples of cooling surfaces can be found at U.S. Pat. No. 5,735,844 and disclosed in U.S. patent application Ser. No. 09/393,830.

Diode cooling unit 28 is used to remove the heat created by laser diodes 24, and typically includes a Peltier cooling device in close proximity to the diode device(s). Alternatively, forced air in conjunction with a diode-mounted heat fin can function as the cooling unit.

Safety shutter 30 is used to ensure no unexpected radiation exposure when the laser system is in the "off" or "standby" state.

Figure 3:
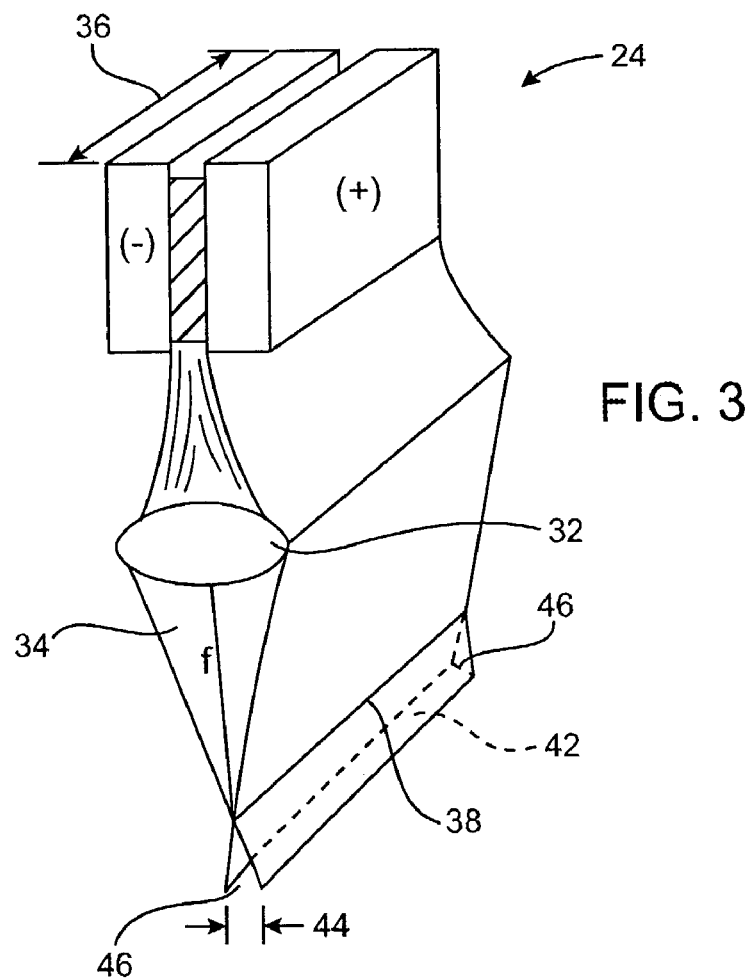
FIG. 3 is a simplified view of the main functional components of a radiation source of FIG. 2 including a laser diode and a focusing rod lens which creates a focal point below the skin surface and creates a elongate rectangular radiation spot having a length about 10 times the width on the skin surface.

With reference now to FIGS. 2 and 3, radiation source 22 is seen to include a laser diode 24 and a cylinder lens 32, the cylinder lens functioning as a main component of the conditioning optics 26. Laser diode 24 is illustrated as a single component for ease of illustration. Laser diode 24 has a length 36 and creates a focal line 38 situated below skin surface 40 so to create a radiation spot 42 at skin surface 40. Radiation spot 42 has a width 44 and has generally the same length, that is length 36, as laser diode 24. Radiation spot 42 preferably has a length to width ratio of at least about 10 to 1, but at least about 5 to 1. By creating a relatively long, narrow radiation spot and by translating the radiation spot perpendicular to its length, the non-therapeutic regions created by radiation beam 34 are minimized. In this way, the problems associated with radiation beam scatter, which includes ineffective heating of the target zone, such as target tissue T, can be substantially reduced. Most radiation scattered parallel to length 36 remains within the heating zone beneath spot 42. Most radiation scattered perpendicular to length 36 heats tissue which has just passed under spot 42 or which will soon pass under spot 42. The regions perpendicular to the length of radiation spot 42, except at the very start and stop of movement, are subjected to full radiation intensity as the beam moves forward. Only at the ends 46 of radiation spot 42 will there be therapeutically ineffective radiation zones such that that tissue is heated but not to a therapeutically effective extent. However, the aggregate area of such ineffectively treated radiation zones are minimized by the configuration and movement of the present invention. Of course during subsequent movements of radiation source 22, those ineffectively treated radiation zones along the edges 46 of radiation spot 42 can be properly heated and treated.

Figure 4:
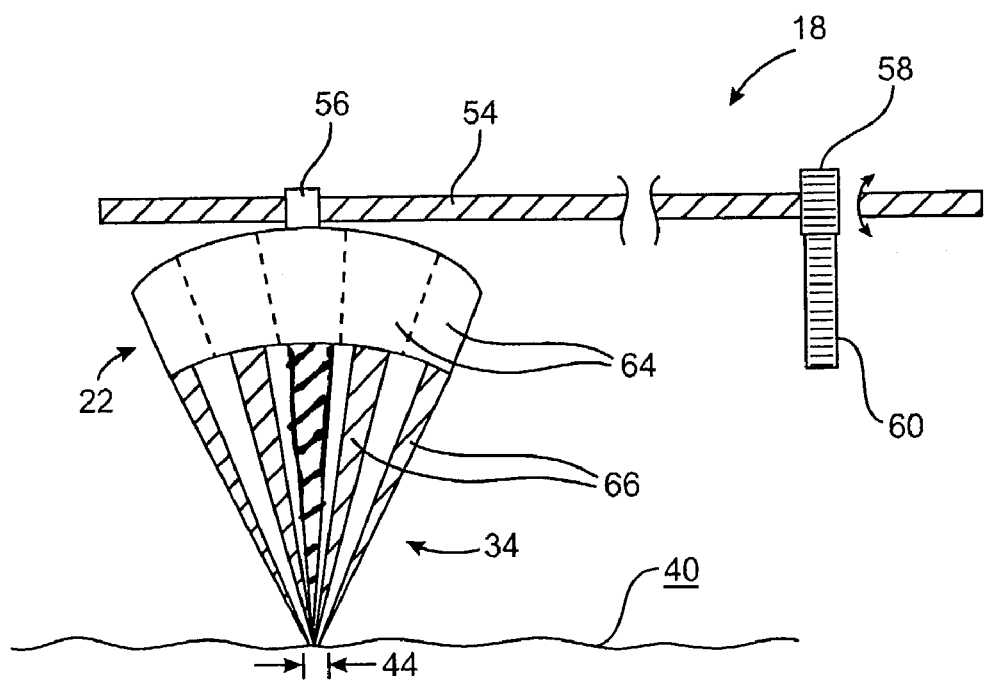
FIG. 4 is a simplified view illustrating a number of radiation sub-sources which constitute the radiation source of FIG. 2 and a mechanical radiation source translator which permits the radiation spot to be controllably translated along the skin surface.

In the present invention it is preferred that radiation source 22 be carried within a housing or body 48, the body having a circumferential skin contacting edge 50 which defines a skin surface plane. Skin surface 40 is assumed to be generally coincident with the skin surface plane. When radiation spot 42 is properly positioned on skin surface 40, radiation source 22 is translated by radiation source translator 18, shown in FIG. 4. Translator 18 includes, for example, a lead screw 54 passing through a threaded boss 56 extending from radiation source 22 and also through a an internally threaded drive nut 58. Drive nut 58 is rotated by a drive gear 60. Both lead screw 54 and drive nut 58 are restrained from moving axially but free to rotate so that rotating drive gear 60 rotates drive nut 58 thus causing lead screw 54 to rotate. This rotation of lead screw 54 causes radiation source 22 to move or translate in the direction of arrow 62. Radiation source 22 of FIG. 4 also is shown to include a number, in this case five, radiation sub-sources 64 each with its own radiation beam component 66, components 66 combining to create radiation beam 34.

Translator 18 may also use a stepper motor, a linear driver, belts and pulleys, a rack and pinion, a linear induction motor or any other conventional or unconventional structure to translate radiation source 18. In addition, translation of radiation source 22 may also be provided by moving body 48 with radiation source 22 housed therein across skin surface 40.

Before beginning treatment, for example hair removal treatment, skin surface 40 may be marked with lines, dots or other markings to help guide placement of radiation delivery module 8 on the skin surface 40. Skin contacting edge 50 of body 48 is placed on skin surface 40 typically with radiation source 22 at one end of body 48. Once properly positioned the user can beginning treatment by entering the proper information using user interface 18. This information may include, for example, hair color, skin color and typical hair shaft diameter. Radiation source 22 is then energized and translator 52 is operated to cause radiation source to move in the direction of arrow 62 over skin surface 40, that is in a direction generally perpendicular to length 36, while irradiating the skin surface along radiation spot 42. After the end of a pass, radiation source 22 can be moved in the opposite direction using transducer 52 if necessary or desired. Radiation spot 42 typically will not extend the full width of body 48 nor traverse the full length of the body. The therapeutically effectively irradiated region may be shown by alignment marks 68 on body 48, see FIG. 2, to help properly align body 48 when an adjacent section of skin surface 40 is to be irradiated.

Effectively controlling the pulse duration as seen by a cross section of dermis requires the dwell time to be controlled. Width 44 and the translation speed will determine the effective pulse duration. The fluence will be determined by the intensity of radiation source 22 within this dimension. Pulse duration can be controlled by, for example, scanning at varied rates.

Modification and variation can be to the disclosed embodiments without departing from the subject invention as defined in the following claims. For example, body 48 may include transparent portions or may be totally transparent. Also, body 48 need not be solid but could be made of mesh and or spaced apart framing members.

Any and all patents, patent applications and printed publications are incorporated by reference.

What is claimed is:

1. A radiation delivery module comprising:
a housing having an open interior region, said housing having a circumferential skin contacting edge supportable over a first skin surface region of a patient;
a radiation source coupled to and mounted within the interior region of the housing and producing a beam of tissue-treating radiation, said radiation beam creating a radiation spot having a length and width, said length being greater than the width; and
a translator coupled to the radiation source which continuously moves the source within the interior region such that the radiation spot is moved relative to the housing in a direction generally perpendicular to the spot length, with the translation speed being selected so that the tissue within said first skin surface region is evenly treated along the path of travel of the spot without moving the housing.

2. The radiation delivery module according to claim 1, wherein:
the length of the radiation spot is at least 5 times the width.

3. The radiation delivery module according to claim 1, wherein:
the length of the radiation spot is at least 10 times the width.

4. The radiation delivery module according to claim 2, wherein:
the housing defines a skin surface plane; and
the radiation beam is directed transverse to and at the skin surface plane.

5. The radiation delivery module according to claim 1, where the radiation source comprises a diode laser.

6. A radiation delivery module comprising:
a housing supportable over a first skin surface region of a patient and defining a skin surface plane;
a radiation source coupled to the housing, the radiation source comprising a plurality of diode laser radiation sub-sources each sub-source creating a radiation beam component, said radiation beam components combining to produce a beam of tissue treating radiation directed transverse to the skin surface plane, said radiation beam creating a radiation spot having a length and a width at the skin surface plane, said length being greater than the width; and
a translator coupled to the radiation source which continuously moves the radiation spot relative to the skin and relative to the housing in a direction generally perpendicular to the spot length, with the translation speed being selected so that the tissue within said first skin surface region is evenly treated along the path of travel of the spot without moving the housing.

7. The radiation delivery module according to claim 6, wherein:
the length of the radiation spot is at least 5 times the width.

8. The radiation delivery module according to claim 6, wherein:
the length of the radiation spot is at least 10 times the width.

* * * * *